(12) United States Patent
Zemp et al.

(10) Patent No.: US 11,150,344 B2
(45) Date of Patent: *Oct. 19, 2021

(54) 3D IMAGING USING A BIAS-SENSITIVE CROSSED-ELECTRODE ARRAY (71) Applicants: Roger Zemp, Edmonton (CA); Christopher Ceroici, Edmonton (CA)

(72) Inventors: Roger Zemp, Edmonton (CA); Christopher Ceroici, Edmonton (CA)

( * ) Notice: Subject to any disclaimer, the term of this patent is extended or adjusted under 35 U.S.C. 154(b) by 477 days.

This patent is subject to a terminal disclaimer.

(21) Appl. No.: 16/148,804

(22) Filed: Oct. 1, 2018

(65) Prior Publication Data
US 2019/0235077 A1 Aug. 1, 2019

Related U.S. Application Data (60) Provisional application No. 62/622,750, filed on Jan. 26, 2018.

(51) Int. Cl.
*G01S 15/89* (2006.01)
*G01S 7/52* (2006.01)
(Continued)

(52) U.S. Cl.
CPC ........ *G01S 15/8925* (2013.01); *A61B 5/0095* (2013.01); *B06B 1/0629* (2013.01);
(Continued)

(58) Field of Classification Search
CPC ............. G01S 15/8925; G01S 7/52019; G01S 7/52046; G01S 7/5209; G01S 7/5206;
(Continued)

(56) References Cited

U.S. PATENT DOCUMENTS 4,448,075 A   5/1984  Takemura
4,580,451 A   4/1986  Miwa
(Continued)

FOREIGN PATENT DOCUMENTS

WO    2008/033528    3/2008

OTHER PUBLICATIONS

Seo, Chi Hyung, and Jesse T. Yen. "A 256 × 256 2-D array transducer with row-column addressing for 3-D rectilinear imaging." IEEE transactions on ultrasonics, ferroelectrics, and frequency control 56, No. 4 (2009): 837-847. (Year: 2009).*

(Continued)

*Primary Examiner* — Daniel Pihulic
(74) *Attorney, Agent, or Firm* — Nathan V. Woodruff (57) ABSTRACT A method and system for imaging a sample uses a 2D array of bias-sensitive, ultrasound transducers arranged in first and second strips, and a source of radiation to stimulate the sample to be imaged. The second electrode strips are sequentially biased according to sequential biasing patterns of voltages that correspond to rows or columns of an invertible matrix. For each biasing pattern, signals are measured from the first electrode strips to detect return signals from the sample that result from the sample being stimulated. A dataset is calculated based on the measured signals, the dataset comprising an effective signal for each of a plurality of transducer elements in the array. An image of the sample is generated based on the dataset.

25 Claims, 5 Drawing Sheets (51) Int. Cl.
*A61B 5/00* (2006.01)
*B06B 1/06* (2006.01)

(52) U.S. Cl.
CPC .......... *G01S 7/5206* (2013.01); *G01S 7/5209* (2013.01); *G01S 7/52019* (2013.01); *G01S 7/52046* (2013.01)

(58) Field of Classification Search
CPC . A61B 5/0095; B06B 1/0629; B06B 2201/20; B06B 1/0207
See application file for complete search history.

(56) References Cited

U.S. PATENT DOCUMENTS

| | | | |
|---|---|---|---|
| 4,671,293 | A | 6/1987 | Shaulov |
| 5,027,820 | A | 7/1991 | Pesque |
| 5,152,294 | A | 10/1992 | Mochizuki |
| 5,327,895 | A | 7/1994 | Hashimoto |
| 5,345,139 | A | 9/1994 | Gururaja |
| 5,410,205 | A | 4/1995 | Gururaja |
| 5,460,179 | A | 10/1995 | Okunuki |
| 5,460,181 | A | 10/1995 | Seyed-Bolorforosh |
| 5,488,956 | A | 2/1996 | Bartelt |
| 5,657,295 | A | 8/1997 | Howard |
| 5,671,746 | A | 9/1997 | Dreschel |
| 5,846,201 | A | 12/1998 | Adams |
| 6,381,197 | B1 | 4/2002 | Savord |
| 6,419,633 | B1 | 7/2002 | Robinson |
| 7,087,023 | B2 | 8/2006 | Daft |
| 7,544,165 | B2 | 6/2009 | Mamayek |
| 7,618,373 | B2 | 11/2009 | Ladabaum |
| 7,780,597 | B2 | 8/2010 | Panda |
| 2007/0079658 | A1 | 4/2007 | Wagner |
| 2007/0206193 | A1 | 9/2007 | Pesach |
| 2011/0054292 | A1 | 3/2011 | Hirson |
| 2018/0164418 | A1* | 6/2018 | Zemp .................. G01S 15/8993 |
| 2019/0235077 | A1* | 8/2019 | Zemp .................. G01S 15/8925 |

OTHER PUBLICATIONS

Novell, Anthony, Mathieu Legros, Jean-Marc Gregoire, Paul A. Dayton, and Ayache Bouakaz. "Evaluation of bias voltage modulation sequence for nonlinear contrast agent imaging using a capacitive micromachined ultrasonic transducer array." Physics in Medicine & Biology 59, No. 17 (2014): 4879. (Year: 2014).*

Rasmussen, M. F., & Jensen, J. A.; 3-D ultrasound imaging performance of a row-column addressed 2-D array transducer: A measurement study; IEEE International Ultrasonics Symposium (IUS); Jul. 2013; pp. 1460-1463.

Sampaleanu, A., Zhang, P., Kshirsagar, A., Moussa, W., & Zemp, R. J.; Top-orthogonal-to-bottom-electrode (TOBE) CMUT arrays for 3-D ultrasound imaging; IEEE transactions on ultrasonics, ferroelectrics, and frequency control; 2014; 61(2); pp. 266-276.

Wang, Y., Guo, Z., Wang, L V., Erpelding, T. N., Jankovic, L., Robert, J. L., & David, G.; In vivo three-dimensional photoacoustic imaging based on a clinical matrix array ultrasound probe; Journal of Biomedical Optics; 2012; 17(6); p. 061208.

Ephrat, P., Keenlislide, L., Seabrook, A., Prato, F. S., & Carson, J. J.; Three-dimensional photoacoustic imaging by sparse-array detection and iterative image reconstruction; Journal of Biomedical Optics; 2008; 13(5); p. 054052.

Chee, R. K., Sampaleanu, A., Rishi, D., & Zemp, R. J.; Top orthogonal to bottom electrode (TOBE) 2-D CMUT arrays for 3-D photoacoustic imaging; IEEE transactions on ultrasonics, ferroelectrics, and frequency control; 2014; 61(8); pp. 1393-1395.

Online advance program for Photonics West 2018 (Jan. 27-Feb. 1, 2018); SPIE website; Oct. 2, 2018.

* cited by examiner

3D IMAGING USING A BIAS-SENSITIVE CROSSED-ELECTRODE ARRAY

FIELD

This relates to imaging, such as photoacoustic or ultrasonic imaging, of an object, and in particular a method and apparatus that uses a bias-sensitive crossed-electrode 2D array for generating 3D images.

BACKGROUND

Photoacoustic imaging is the process of using acoustic waves generated from the absorption of electromagnetic energy to form images, while ultrasonic imaging stimulates the sample using ultrasonic energy. Ultrasonic imaging investigates mainly the mechanical properties of tissue, and photoacoustic imaging allows for the probing of optical properties such as oxygen saturation in blood vessels while allowing for deeper imaging depths than optical-only imaging.

Receiving photoacoustic signals on a 2D transducer array allows for the reconstruction of a 3D volume using dynamic receive beamforming. However, a limitation in this approach is the size of a fully-connected 2D array. For example, an array with a size of 64×64 would have 4,096 transducer elements. This would require 4,096 receive channels which would become impractical due to wiring congestion as well as prohibitively expensive. An alternative approach is using a cross-electrode or Top-Orthogonal-to-Bottom-Electrode (TOBE) wiring scheme. In a TOBE array, top transducer electrodes are all connected along columns while bottom connections are connected along rows. This allows for the addressing of elements in the array by transmitting/receiving along rows/columns with a greatly reduced channel count. A 64×64 TOBE array requires only 128 channels. In addition, bias sensitive transducers such as Capacitive Micromachined Ultrasound Transducers (CMUTs) or bias-sensitive piezoelectric arrays allow for additional types of operation by switching array biases. For example, the signal for a single element in a bias-sensitive 2D array can be obtained by biasing the corresponding column and receiving from the corresponding row. Unbiased elements will not receive signals and so will not contribute to the signals received at the connected row.

Another strategy is to bias a single column and then receiving along all rows. By biasing a single column and receiving along a single row, only the biased element along the row will contribute a signal and therefore be isolated. This approach may be used for photoacoustic imaging. By biasing a single column while grounding all others and receiving across all rows, the signals from the single biased elements in each row are sampled. The bias is then stepped across all columns in the array, effectively acquiring a dataset equivalent to a fully-connected array. As only a small fraction of the elements are actively receiving signals at a given time, this may result in a poor signal-to-noise ratio (SNR).

SUMMARY

According to an aspect, there is provided a method of imaging a sample, comprising the steps of: providing a 2D array of bias-sensitive, ultrasound transducers, each ultrasound transducer having first and second electrodes on opposite sides of a transducer element, the respective first electrodes being connected in plural first electrode strips, and the respective second electrodes being connected in plural second electrode strips, the plural first electrode strips being oriented at an angle to the plural second electrode strips, the angle being substantially different from zero; stimulating the sample to be imaged using an incident radiation source; sequentially biasing the second electrode strips according to sequential biasing patterns of voltages that correspond to rows or columns of an invertible matrix; for each biasing pattern, measuring signals from the first electrode strips to detect return signals from the sample that result from the sample being stimulated; and calculating a dataset based on the measured signals, the dataset comprising an effective signal for each of a plurality of transducer elements in the array; generating an image of the sample based on the dataset.

According to other aspects, the method may further comprise one or more of the following elements, alone or in combination: calculating the dataset may comprise applying the invertible matrix to the measured signals; the incident radiation source may be electromagnetic; the transducer elements may comprise an electrostrictive, piezoelectric, electrostrictive relaxor or piezoelectric relaxor material, and one or more biasing patterns comprise both positive and negative voltages; the array of ultrasound transducers may comprise capacitive micromachined ultrasound transducers; the incident radiation source may be ultrasonic, the ultrasound transducers may be connected to transmit and receive ultrasonic signals, and the polarity and amplitude of the emitted signals from each transducer element are dependent on the polarity and strength of the respective bias voltages; the 2D array may define a planar or curved surface; measuring the signal may comprise decoupling a received AC signals from the bias; the second electrode strips may be biased with the biasing pattern when the return pulses are measured; the sensitivity of the ultrasound transducer may be related to the bias voltage; and the matrix may be a Hadamard matrix or an S-matrix.

According to an aspect, there is provided an imaging system comprising a 2D array of bias-sensitive ultrasound transducers. Each ultrasound transducer has a first electrode on a first side of a transducer element and a second electrode on a second side of the transducer element. The respective first electrodes are connected in plural first electrode strips, and the respective second electrodes are connected in plural second electrode strips. The plural first electrode strips are oriented at an angle to the plural second electrode strips that is substantially different from zero. A source of radiation is incident on a sample to be imaged and is configured to cause the sample to generate an ultrasonic response. A controller is connected to the first and second electrode strips that is programmed to: sequentially bias the second electrode strips according to a sequential biasing pattern of voltages that correspond to rows or columns of an invertible matrix; for each biasing pattern, measure signals from the first electrode strips to detect return signals from the sample that result from the sample being stimulated; calculate a dataset based on the measured signals, the dataset comprising an effective signal for each of a plurality of transducer elements in the array; and generate an image of the sample based on the dataset.

According to other aspects, the system may further comprise one or more of the following elements, alone or in combination: the controller may be programmed to calculate the dataset by applying the invertible matrix to the measured signals; the incident radiation source may be electromagnetic; the transducer elements may comprise an electrostrictive, piezoelectric, electrostrictive relaxor or piezoelectric relaxor material and one or more biasing patterns comprise both positive and negative voltages; the array of ultrasound transducers may comprise capacitive micromachined ultrasound transducers; the incident radiation source may be ultrasonic; the ultrasound transducers may be connected to transmit and receive ultrasonic signals, and the polarity and amplitude of the emitted signals from each transducer element may be dependent on the polarity and strength of the respective bias voltages; the 2D array may define a planar or curved surface; the first and second electrodes may comprise top and bottom electrodes or bottom and top electrodes; the system may further comprise bias tees for decoupling a received AC signal from the bias for each measured signal strength; and the matrix may be a Hadamard matrix or an S-matrix.

According to an aspect, there is provided a 3D imaging technique using 2D crossed-electrode, or Top-Orthogonal to Bottom-electrode (TOBE) arrays with bias-pattern encoding to maximize signal-to-noise ratio while minimizing the number of channels needed. The array may be a 2D grid of transducers, each with a top and bottom electrode. Each array column connections connects the top electrodes while each row connection connects the bottom electrodes. The elements are bias sensitive, meaning they will only receive photoacoustic signals and produce electrical output signals when a bias is applied across the top and bottom electrodes.

According to an aspect, there is provided a photoacoustic imaging scheme. A laser may be used to generate photoacoustic signals at the location of the phantom or tissue. A set of bias patterns may then applied to the column electrodes. These biases may comprise positive and negative voltages in a pattern derived from the row vectors of an invertible matrix, such as the Hadamard matrix. Signals may then be read out through row connections. After receiving row signals for every bias pattern vector in the invertible encoding matrix, the received dataset may then be "decoded" by multiplying this dataset by the inverse of the encoding matrix. The result is a dataset equivalent to the case of where a single column is biased for each imaging event and all other columns were grounded. Since in this dataset there is only one active element per row, the signal for each element in the array may be obtained and a 3D reconstruction of the photoacoustic data may be generated using dynamic receive beamforming. Although the decoded dataset has only a single active element per row, the actual acquired dataset has all row elements biased in some pattern. This means that the SNR is greatly improved since the entire array is used for sensing photoacoustic signals for the entire imaging sequence, in contrast, activating a single biased column at a time stepped across the array produced much poorer SNR. The role of the rows and columns may be interchanged.

According to an aspect, there is provided an imaging system having a bias-sensitive crossed-electrode 2D ultrasound transducer array. In describing the array as "2D", it will be understood that this refers to the way in which the transducers are connected together, and not necessarily the shape of the array as a whole. In particular, the 2D array need not define a planar surface, but may also define a curved surface, such as a parabolic or semi-spherical shape. The electrode array may be constructed from capacitive micromachined ultrasound transducers. The electrode array may be constructed from a piezoelectric material or electrostrictive material, such as piezoelectric or electrostrictive relaxor material. The array elements may be capable of transmitting ultrasonic signals as well as receiving ultrasonic signals. The transducers may be capable of amplitude-and/or phase-modulation. This may be accomplished by controlling the amplitude and polarity of an applied bias voltage, respectively. Top electrodes are connected in strips orthogonal to (or at a substantially different angle than) bottom electrode strips, and these strips interconnect individual transducer elements. A particular transducer element may be addressed by biasing the appropriate row and column.

In a photoacoustic mode of operation, an incident electromagnetic radiation source (e.g. flashlamp, microwave, laser, such as a pulsed or intensity modulated laser, etc.) is used to stimulate a sample to be imaged. Bias voltages are applied to the rows or columns of the array using a controller. For a given detection event, such as each radiation pulse incident on the sample, the bias voltages are applied using a bias voltage pattern applied by a controller. The bias voltage patterns are selected according to an invertible coding matrix, excluding the identity matrix, such as a Hadamard Matrix. The bias voltage pattern may have both positive and negative polarities and may also include zeros.

The detection event may involve measuring signal strength from the rows of the matrix (or the columns, if the biasing patter is applied to the rows). A set of amplifiers and data acquisition electronics may be used to acquire data for each detection event from the rows or columns of the array. A processor may be used to decode the aperture encoding using the inverse of the coding matrix, and to perform image reconstruction or beamforming to create (3D) images.

In another example, a bias-sensitive piezoelectric transducer arrays (relaxor arrays) for 3D photoacoustic imaging fabricated using a dice-and-fill approach may be used. A row-column connection scheme allows for significantly reduced channel counts. 3D photoacoustic imaging capabilities may be achieved with a 10 MHz 64×64 element array using a pulsed laser incident on 25.4 µm diameter wire phantoms. In one example, after reconstruction of the 3D images using a Hadamard bias encoding technique, the lateral and elevational resolutions were estimated as 0.6 mm and 0.5 mm, close to theoretically-expected resolution, 0.4 mm.

In another example, there is provided bias-sensitive piezoelectric transducer arrays for 3D photoacoustic imaging. A PMN-PT electrostrictive relaxor material may be developed into a 1-3 composite 10-MHz transducer using a dice-and-fill approach. The transducers may be fabricated into a 2D 64×64 lambda-pitch array with a Top-Orthogonal-to-Bottom-Electrode (TOBE) wiring configuration where all top electrodes are connected along columns and all bottom electrodes along rows. This allows for indexing across the entire array with a greatly reduced channel count compared to a fully wired array. By biasing a column and receiving along a row, individual elements may be isolated for readout of signals from all elements using bias-switching-based multiplexing. Photoacoustic 3D imaging experiments using this 64×64 element relaxor array were conducted with a pulsed excitation Nd:YAG laser incident on two crossed wires with 25.4 µm diameters. The 3D image of these wire phantoms was reconstructed using a technique called Hadamard encoding in which, rather than using a single column to index an array element, multiple columns are biased simultaneously allowing for more receiving elements. The channel data was then decoupled to estimate the signals from each element of the 2D array. These data were then beamformed to reconstruct 3D images. In this example, it was found that the Hadamard biasing scheme improves SNR by nearly a factor of N for an N×N array. Lateral and elevational resolutions were estimated as 0.6 mm and 0.5 mm, close to theoretically-expected resolution, 0.4 mm.

BRIEF DESCRIPTION OF THE DRAWINGS

These and other features will become more apparent from the following description in which reference is made to the appended drawings, the drawings are for the purpose of illustration only and are not intended to be in any way limiting, wherein.

DESCRIPTION OF PREFERRED EMBODIMENTS

There will now be described a 3D imaging technique that utilizes bias encoding to allow for a transducer array to receive signals in a way that may allow for an improved SNR. In the discussion below, rows and columns of the matrix are identified as a matter of convenience or convention. However, what is considered a row or column may be interchangeable, and more importantly, the purpose of each of the lines of transducers, either in rows or columns may be interchanged in the process described herein.

The imaging technique described below may be applied to photoacoustic imaging, where the sample is stimulated using electromagnetic radiation, or ultrasonic imaging, where the sample is stimulated using ultrasonic energy. As will be recognized and based on known imaging strategies, various imaging approaches may be used to stimulate the sample and detect ultrasound energy using a 2D array.

Figure 2:
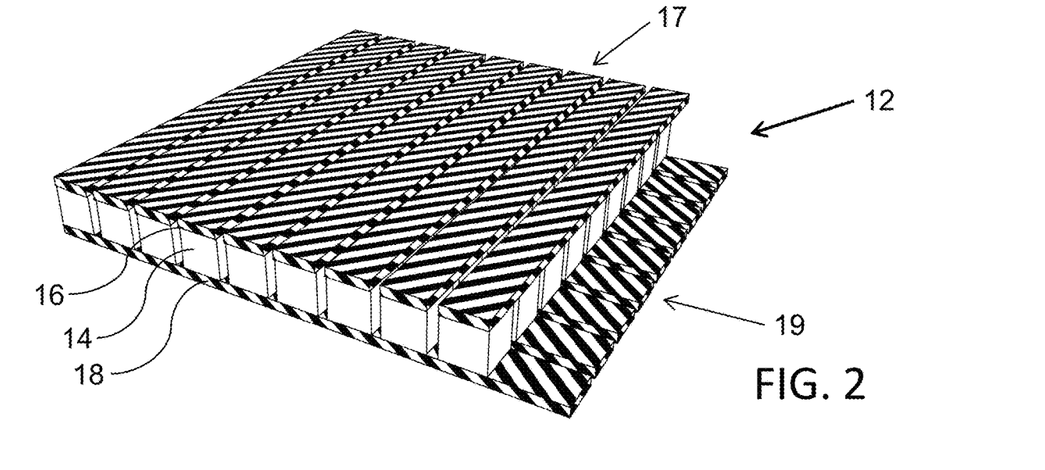
FIG. 2 is a perspective view of a transducer array.

In general, the method and system used herein includes a 2D array of bias-sensitive, ultrasound transducers 14, as shown in FIG. 2, where the array is indicated generally by reference number 12. Array 12 is shown as being planar, but it may also be curved, such as parabolic in one or two dimensions, or semi-spherical, as it known in the art. Transducers 14 may be capacitive micromachined ultrasound transducers or other types of transducers. Transducers 14 may be made from piezoelectric material, electrostrictive material, piezoelectric or electrostrictive relaxor material, or any other suitable material that may be known in the art. Another example of a 2D array used for ultrasonic imaging is described in U.S. patent application Ser. No. 15/792,422 (Zemp) entitled "System and method for ultrasound imaging", the teachings of which are incorporated herein by reference.

Each ultrasound transducer 14 has first and second electrodes 16 and 18 on opposite sides of a transducer element 20. The respective first electrodes 16 are connected in plural first electrode strips 17, and the respective second electrodes 18 are connected in plural second electrode strips 19. The first strips 17 are oriented at an angle to the second strips 19 at an angle that is substantially different from zero. Typically, this will be perpendicular, or near perpendicular.

The arrangement of transducer array 12 relative to a radiation source, sample, and the corresponding electronics may be constructed and defined according to common design principles as known by those skilled in the art.

Figure 1:
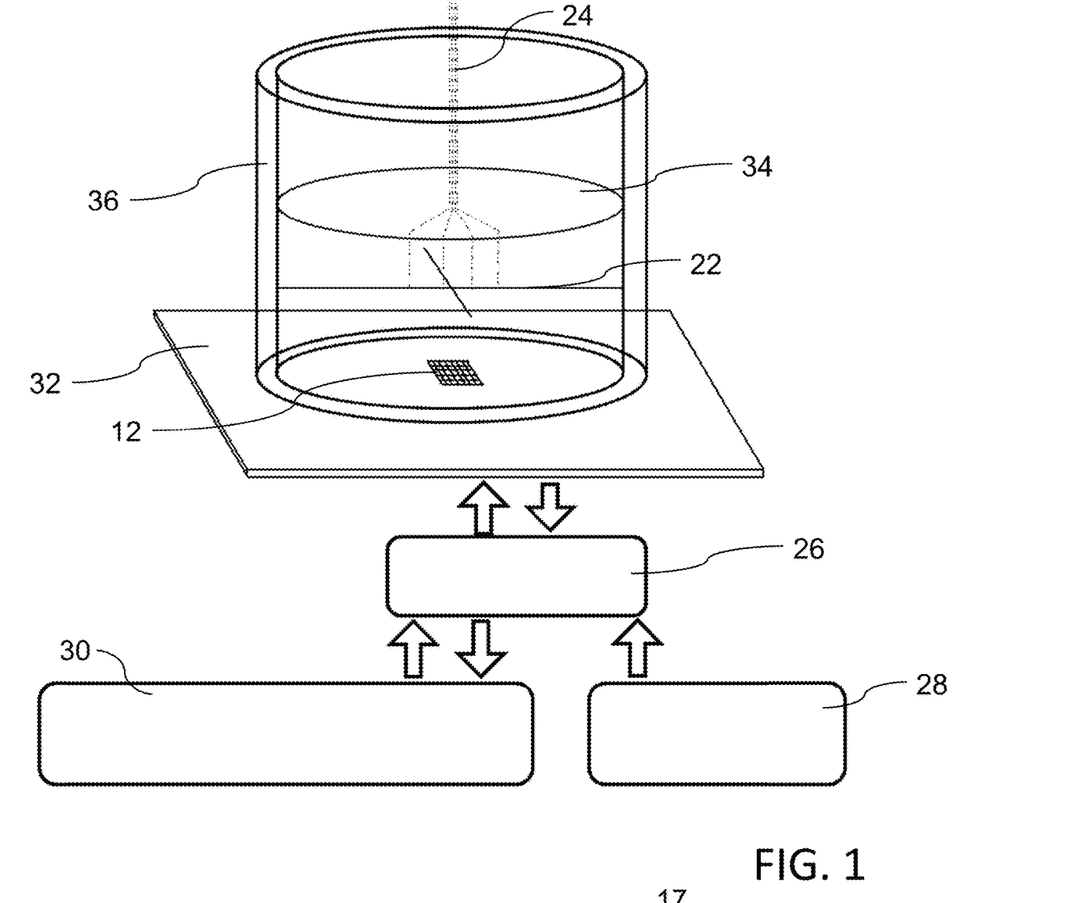
FIG. 1 is a schematic view of an imaging system.

Referring to FIG. 1, an example of a setup is shown that was used to obtain experimental results described below. As shown, array 12 is placed on an interface PCB 32 adjacent to a sample 22 to be imaged using an incident radiation source 24. This may be a laser as depicted, but may be other radiation sources, as discussed above. In the depicted example, sample 22 is located in an intralipid solution 34 to simulate scattering that would be encountered in a typical sample, but would not be present in actual applications. Also as shown, radiation source 24 is opposite array 12 relative to sample 22. However, it will be understood that radiation source 24 may be on the same side as, or space laterally from, sample 22.

As will be discussed below, as sample 22 is stimulated, second electrode stripes 19 are biased and signals are measured from the first electrode strips 17 to detect return signals from sample 22 that result from the sample being stimulated. The signals are routed through a bias tee 26, which is connected to a DC bias control 28 and a controller 30. These signals are then processed to calculate an image of the sample. In the event that the system is used in an ultrasound imaging system, transducers 14 may be connected to both transmit and receive ultrasonic signals, as will be known in the art. For example, the polarity and amplitude of the emitted signals from each transducer element may be dependent on the polarity and strength of the respective bias voltages applied to each transducer 14. Typically, the second electrode strips 19 will be biased with the biasing pattern when the return pulses are measured, and measuring the signal may involve decoupling a received AC signal from the bias, depending on how transducers 14 are biased. Generally speaking, the sensitivity of the ultrasound transducer is related to the bias voltage, which allows the measured signal to be varied based on a bias pattern applied to array 12, as is described below.

The present method and system uses a different approach to biasing and receiving signals using array 12. Rather than receive along a single biased column of elements j to obtain signals $x_{0j}(t), x_{1j}(t), \ldots x_{ij}(t), \ldots x_{ij}(t)$, where i is the row number, all columns are biased using a bias pattern chosen from the rows of an invertible matrix, such as a Hadamard matrix, consisting of ±1s. Each bias pattern is applied to column biases and the row electrode information (or vice versa) is measured providing the dataset W(t):

$$W(t) = \begin{bmatrix} w_0^0(t) & w_1^0(t) & \ldots & w_N^0(t) \\ w_0^1(t) & w_1^1(t) & \ldots & w_N^1(t) \\ \vdots & \vdots & & \vdots \\ w_0^B(t) & w_1^B(t) & \ldots & w_N^B(t) \end{bmatrix}$$

N is the total number of rows while B is the number of bias patterns, equal to the number of rows in the invertible matrix. Each measured signal $w_i^b(t)$ for row i and bias pattern b consists of the superimposed signals of all elements in row i multiplied by the respective column bias pattern value $h_j(b)$.

$$w_i^b(t) = x_{i0}(t)h_0(b) + \ldots x_{iN}(t)h_B(b)$$

Figure 3:
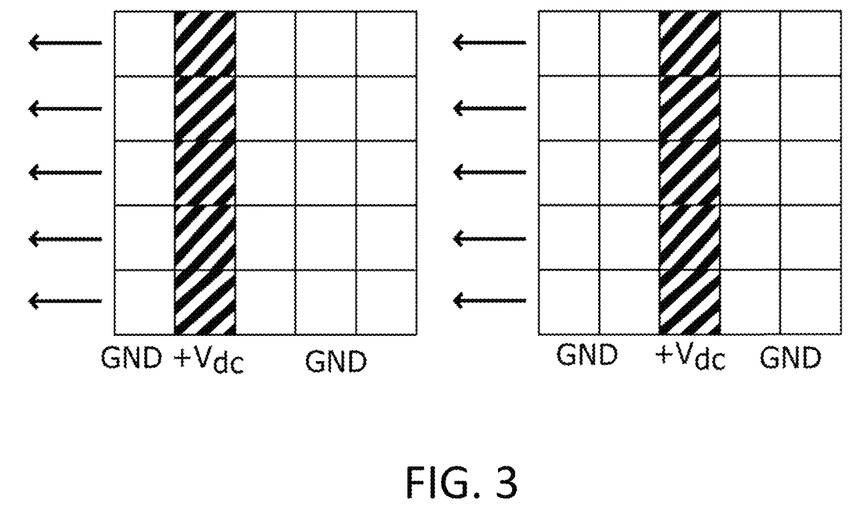
FIGS. 3 and 4 are to plan views of biasing patterns for an array of transducers.
Figure 4:
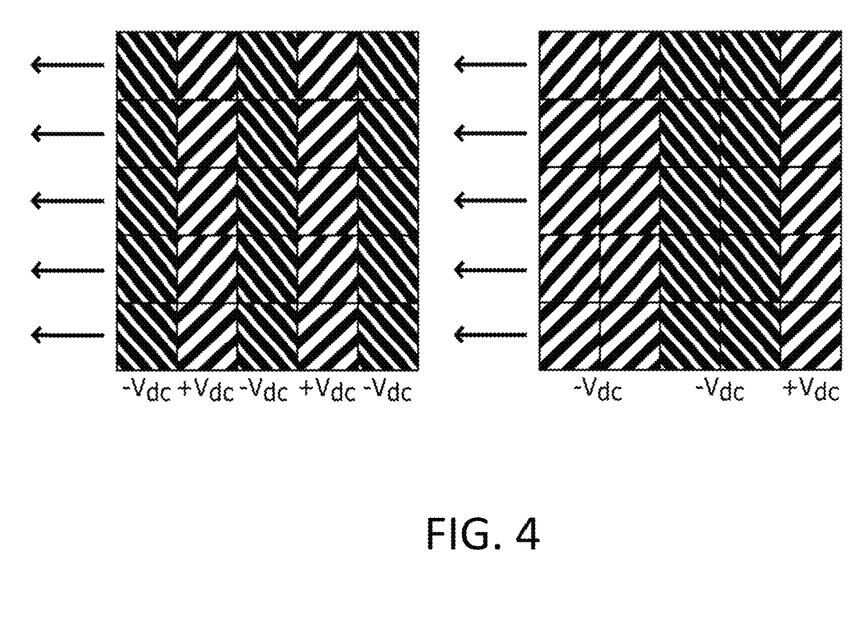

Referring to FIG. 3, examples of biasing patterns are shown, which allows for all elements in an array to acquire signals for every imaging event. As shown, rather than biasing a single column at a time as in FIG. 1, a bias pattern consisting of +/− is applied across columns. These patterns are selected from the rows of an invertible matrix. Typically, the number of detection events and bias patterns applied will correspond with the number of rows or columns in the invertible matrix, such that, when the mathematical operations are performed, a value for each transducer may be obtained. However, in comes cases, values for only a subset of transducer elements may be sought, or some values may be predetermined or approximated, in which case the number of detection events may be reduced.

The dataset may also be characterized by the following formula:

$$W(t) = \begin{bmatrix} w_1^1(t) & \cdots & w_N^1 \\ \vdots & \ddots & \vdots \\ w_1^N & \cdots & w_N^N \end{bmatrix} = \begin{bmatrix} x_1^1(t) & \cdots & x_N^1(t) \\ \vdots & \ddots & \vdots \\ x_1^N(t) & \cdots & x_N^N \end{bmatrix} \begin{bmatrix} h_1^1 & \cdots & h_N^1 \\ \vdots & \ddots & \vdots \\ h_1^N & \cdots & h_N^N \end{bmatrix} + N(t)$$

where $w_j^i(t)$ is the signal trace measured by row i during transmit event j, $x_j^i(t)$ is the signal from row i when only a single bias is applied at column j, $h_j^i$ is the bias weight applied to element i during transmit event j, and $N(t)$ is the noise associated with each channel.

In order to retrieve a dataset consisting of only the individual element signals X(t), the bias-encoded dataset W(t) may be decoded by multiplying it with the inverted matrix H $$X(t) = W(t)H^{-1}$$

The received element data in X(t) can then be used to reconstruct a 3D image using dynamic receive beamforming. These techniques are known in the art, and will not be described further.

Imaging is done using known imaging equipment and arrangements. The actual equipment used will depend on the type of imaging (e.g. photoacoustic vs. ultrasound imaging), and the sample being imaged. For example, for an electromagnetic source of radiation, it is common to use a laser with a desired wavelength,

EXAMPLES

Figure 5:
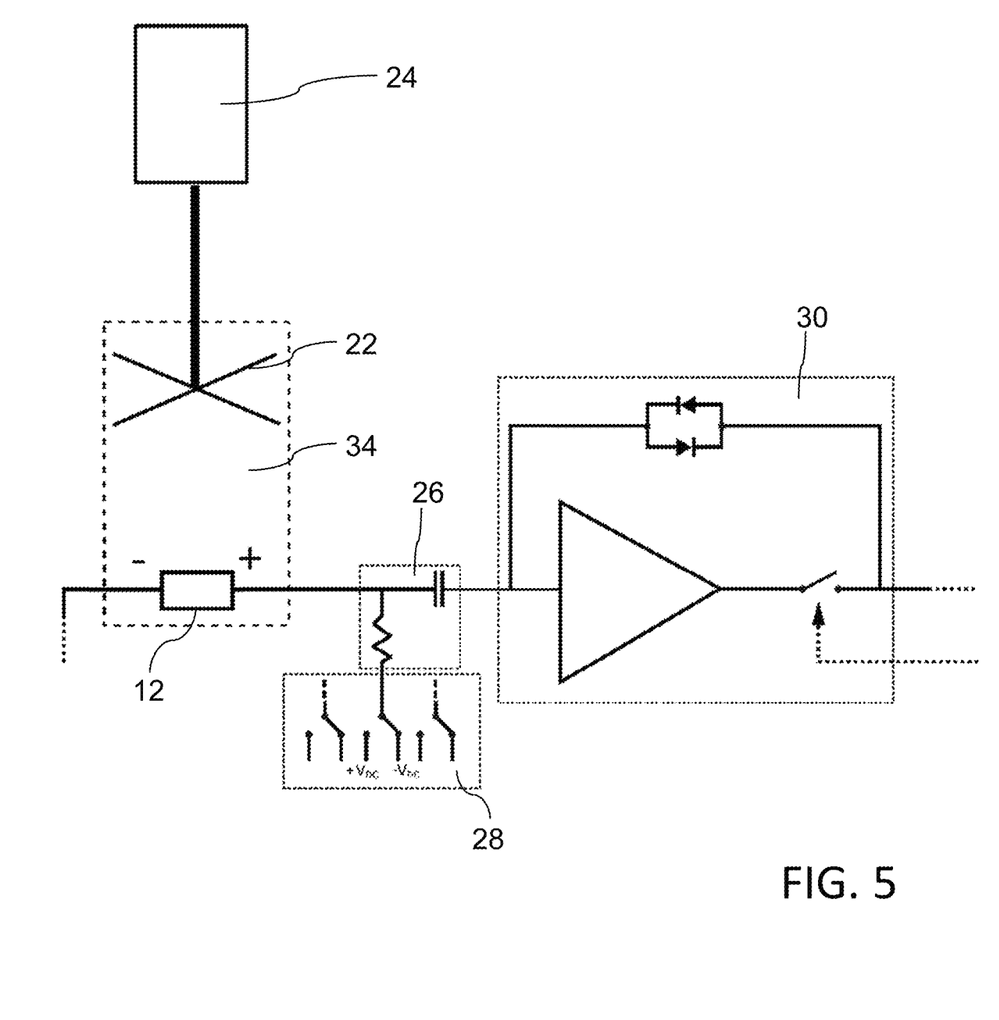
FIG. 5 is a schematic of an experimental setup used to image the crossed-wire phantoms.

In one example, an experiment was conducted using a 64×64 element relaxor array which was developed into a 1-3 composite 10-MHz transducer using a dice-and-fill approach. The experimental setup is shown in FIGS. 1 and 5. Referring to FIG. 1, array 12 was wire bonded to a PCB 32, which was then interfaced to a bias tee 26, connecting a relay-based bias switching board 28 and a controller 30, which includes receive preamplifiers, and a Verasonics experimental ultrasound system for performing analog-to-digital conversion. A glass tank 36 was attached to the PCB with two 17.8 μm-diameter aluminum wire phantoms 22 attached in a cross shape with a 1 mm spacing at the intersection and a 12.8 mm spacing between the first wire and the array. The tank was filled with a 1% intralipid solution 34 to simulate optical scattering medium such as tissue. The bottom wire was 12.8 mm above the array surface. Radiation source 24 was a Nd:YAG laser 532 nm pulsed beam with a 79.2 mJ/cm² fluence, directed towards the wire intersection 22.

Imaging sequences were conducted using a single biased column stepped across the array and acquiring signals across all rows, i.e. equivalent to replacing the invertible matrix with an identify matrix in the equations above, as well as using Hadamard-encoded bias patterns. Bias patterns were programmed using a microcontroller which switched an array of relays between ±50 V for each column electrode. Images were then reconstructed by using delay-and-sum beamforming in 3D.

Figure 6:
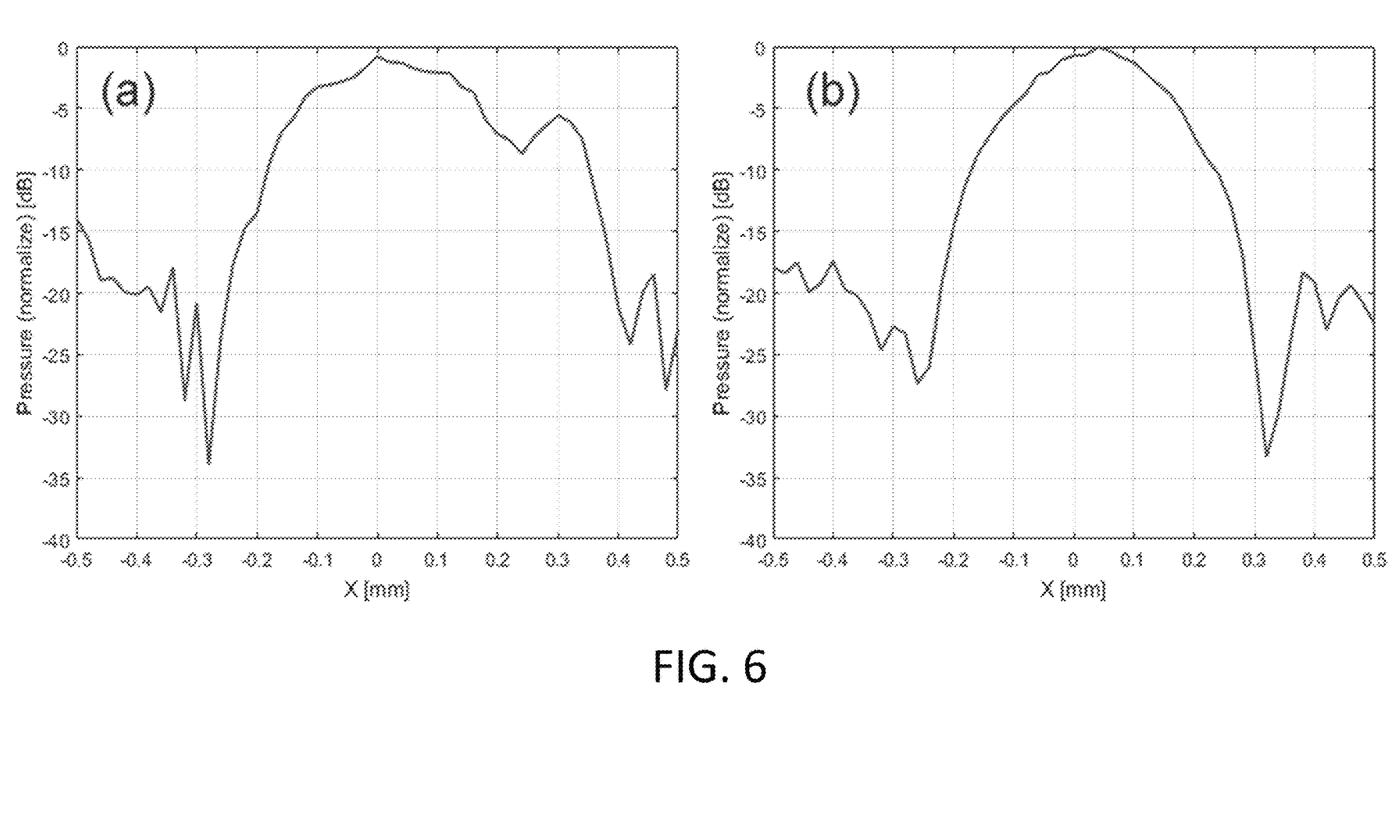
FIG. 6 compares X-axis point spread function of crossed-wire phantoms imaged using (a) single-column biasing and (b) Hadamard-encoded biasing.

FIG. 6 depicts the X-axis point spread function of wire using a single-column biasing strategy, as shown in graph (a) compared to a Hadamard-encoded biasing strategy, as shown in graph (b). The Hadamard-encoded bias scheme demonstrated an azimuthal Full width at half maximum (FWHM) resolution of 369 μm while the single-column bias technique had a FWHM resolution of 396 μm.

Figure 7:
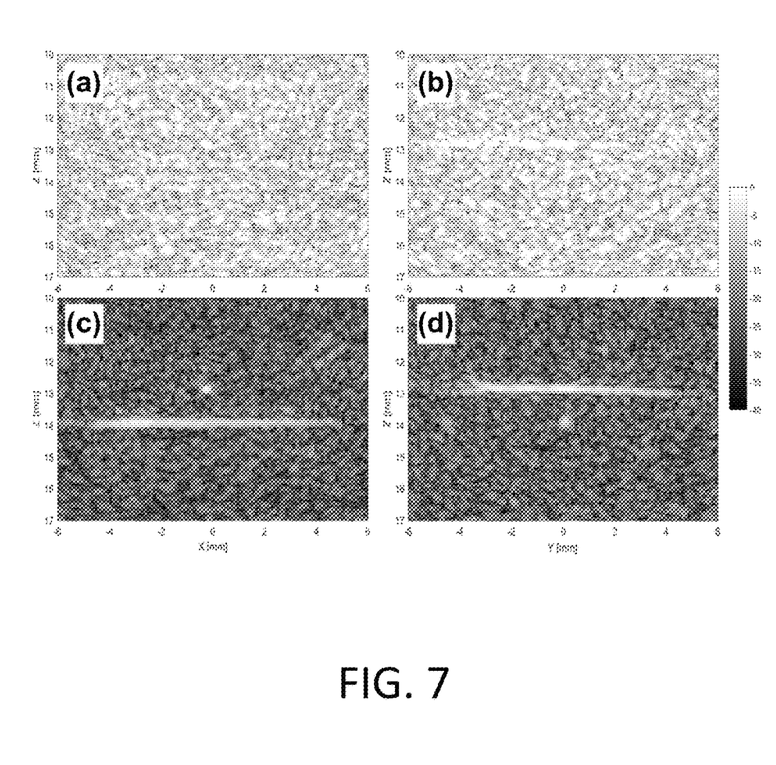
FIG. 7 compares XZ-plane reconstructions of the crossed-wire phantoms using (a) single-column biasing and (c) Hadamard-encoded biasing, and YZ-plane reconstructions using (b) single-column biasing and (d) Hadamard-encoded biasing.

FIG. 7 shows reconstructed images of the crossed-wire phantoms. FIGS. 7a and 7b show the XZ-plane reconstructed images of the crossed-wire phantoms using single-column biasing and Hadamard-bias-encoding, respectively, while FIGS. 7c and 7d show the YZ-plane reconstructions using single-column biasing and Hadamard-encoded biasing, respectively. The Hadamard-encoded bias scheme demonstrated an azimuthal Full width at half maximum (FWHM) resolution of 369 μm while the single-column bias technique had a FWHM resolution of 396 μm. The signal-to-noise ratio of the Hadamard-encoded bias reconstruction was 24.6 dB while the single-column biasing reconstruction had an SNR of 15.9 dB.

The imaging performance of both biasing schemes is summarized in Table I below:

TABLE I

Summary of Imaging Results

|  | Identity Matrix Bias Pattern | Hadamard Matrix Bias Encoding |
| --- | --- | --- |
| Axial Resolution (μm) | 250 | 220 |
| Elevational Resolution (μm) | 396 | 369 |
| Azimuthal Resolution (μm) | 487 | 311 |
| SNR (dB) | 15.9 | 24.6 |

Figure 8:
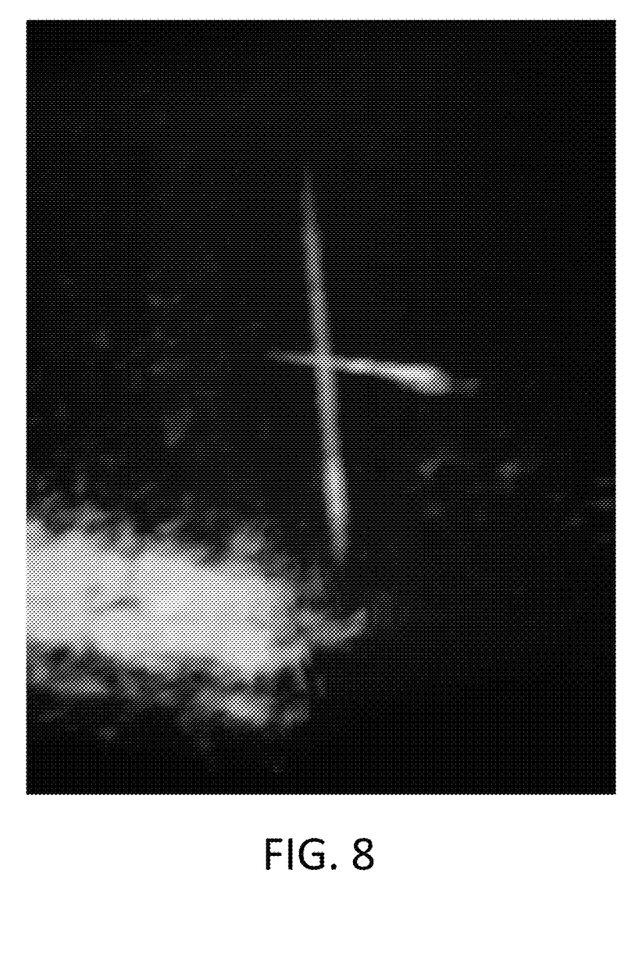
FIG. 8 depicts a reconstruction of the cross-wires in scattering medium using a Hadamard-encoded bias sequence.

By reconstructing with 61 azimuthal lines and 31 elevational lines, a 3D reconstruction of the crossed wires was obtained, as shown in FIG. 8.

The use of Hadamard-bias encoded imaging as described in this example allows for acquisition across the whole array during the entire imaging sequence while also acquiring signals from all individual elements through the use of mathematical decoding. As a result, substantial SNR and resolution benefits were observed when compared with the single-column biasing approach.

In other examples the imaging speed may be increased by using solid-state switching circuitry for bias sequence programming rather than relays. In addition, larger TOBE arrays may be used without a substantial increase in channel count.

The invention claimed is:

1. A method of imaging a sample, comprising the steps of:
providing a 2D array of bias-sensitive, ultrasound transducers, each ultrasound transducer having first and second electrodes on opposite sides of a transducer element, the respective first electrodes being connected in plural first electrode strips, and the respective second electrodes being connected in plural second electrode strips, the plural first electrode strips being oriented at an angle to the plural second electrode strips, the angle being substantially different from zero;

stimulating the sample to be imaged using an incident radiation source;

sequentially biasing the second electrode strips according to sequential biasing patterns of voltages that correspond to rows or columns of an invertible matrix;

for each biasing pattern, measuring signals from the first electrode strips to detect return signals from the sample that result from the sample being stimulated;

calculating a dataset based on the measured signals, the dataset comprising an effective signal for each of a plurality of transducer elements in the array; and generating an image of the sample based on the dataset.

2. The method of claim 1, wherein calculating the dataset comprises applying the invertible matrix to the measured signals.

3. The method of claim 1, wherein the incident radiation source is electromagnetic.

4. The method of claim 1, wherein the transducer elements comprise an electrostrictive, piezoelectric, electrostrictive relaxor or piezoelectric relaxor material, and one or more biasing patterns comprise both positive and negative voltages.

5. The method of claim 1, wherein the array of ultrasound transducers comprises capacitive micromachined ultrasound transducers.

6. The method of claim 1, wherein the incident radiation source is ultrasonic.

7. The method of claim 6, wherein the ultrasound transducers are connected to transmit and receive ultrasonic signals.

8. The method of claim 7, wherein the polarity and amplitude of the emitted signals from each transducer element are dependent on the polarity and strength of the respective bias voltages.

9. The method of claim 1, wherein the 2D array defines a planar or curved surface.

10. The method of claim 1, wherein measuring the signal comprises decoupling a received AC signals from the bias.

11. The method of claim 1, wherein the second electrode strips are biased with the biasing pattern when the return pulses are measured.

12. The method of claim 1, wherein the sensitivity of the ultrasound transducer is related to the bias voltage.

13. The method of claim 1, wherein the matrix is a Hadamard matrix or an S-matrix.

14. An imaging system comprising:

a 2D array of bias-sensitive ultrasound transducers, each ultrasound transducer having a first electrode on a first side of a transducer element and a second electrode on a second side of the transducer element, the respective first electrodes being connected in plural first electrode strips, and the respective second electrodes being connected in plural second electrode strips, the plural first electrode strips being oriented at an angle to the plural second electrode strips, the angle being substantially different from zero;

a source of radiation that is incident on a sample to be imaged and is configured to cause the sample to generate an ultrasonic response;

a controller connected to the first and second electrode strips, the controller being programmed to:
  sequentially bias the second electrode strips according to a sequential biasing pattern of voltages that correspond to rows or columns of an invertible matrix;
  for each biasing pattern, measure signals from the first electrode strips to detect return signals from the sample that result from the sample being stimulated;
  calculate a dataset based on the measured signals, the dataset comprising an effective signal for each of a plurality of transducer elements in the array;
  generate an image of the sample based on the dataset.

15. The system of claim 14, wherein the controller is programmed to calculate the dataset by applying the invertible matrix to the measured signals.

16. The system of claim 14, wherein the incident radiation source is electromagnetic.

17. The system of claim 14, wherein the transducer elements comprise an electrostrictive, piezoelectric, electrostrictive relaxor or piezoelectric relaxor material and one or more biasing patterns comprise both positive and negative voltages.

18. The system of claim 14, wherein the array of ultrasound transducers comprises capacitive micromachined ultrasound transducers.

19. The system of claim 14, wherein the incident radiation source is ultrasonic.

20. The system of claim 14, wherein the ultrasound transducers are connected to transmit and receive ultrasonic signals.

21. The system of claim 20, wherein the polarity and amplitude of the emitted signals from each transducer element is dependent on the polarity and strength of the respective bias voltages.

22. The system of claim 14, wherein the 2D array defines a planar or curved surface.

23. The system of claim 14, wherein the first and second electrodes comprise top and bottom electrodes or bottom and top electrodes.

24. The system of claim 14, further comprising bias tees for decoupling a received AC signal from the bias for each measured signal strength.

25. The system of claim 14, wherein the matrix is a Hadamard matrix or an S-matrix.

* * * * *